United States Patent [19]

Ohnsorge et al.

[11] 4,189,433

[45] Feb. 19, 1980

[54] 4-HYDROXY-1,2-BENZISOTHIAZOLES AND THEIR MANUFACTURE

[75] Inventors: Ulrich Ohnsorge, Goennheim; Helmut Hagen, Frankenthal; Fritz-Frieder Frickel, Ludwigshafen, all of Fed. Rep. of Germany

[73] Assignee: BASF Aktiengesellschaft, Fed. Rep. of Germany

[21] Appl. No.: 871,548

[22] Filed: Jan. 23, 1978

[30] Foreign Application Priority Data

Feb. 5, 1977 [DE] Fed. Rep. of Germany ....... 2704793

[51] Int. Cl.$^2$ .................. A61K 31/425; C07D 275/04
[52] U.S. Cl. ..................................... 548/207; 424/270
[58] Field of Search ..................................... 260/304 A

[56] References Cited

U.S. PATENT DOCUMENTS 3,997,548  12/1976  Singerman ..................... 260/304 A

FOREIGN PATENT DOCUMENTS 1058822  2/1967  United Kingdom ................ 260/288 R

OTHER PUBLICATIONS

Haddock, E. and P. Kirby, J. Chem. Soc., 1971, pp. 3994–3999.
Becke F. and H. Hagen, Liebigs Ann. Chem., 729, 146–151 (1969).
Justus Liebigs Annalen der Organishe Chemie, Band 27, p. 280.

Primary Examiner—Alton D. Rollins
Assistant Examiner—Lisa Jones
Attorney, Agent, or Firm—Keil & Witherspoon

[57] ABSTRACT

The new compound 4-hydroxy-1,2-benzisothiazole and its derivatives, and their manufacture. The products are intermediates for new drugs which are useful in cardiac and circulatory disorders.

6 Claims, No Drawings

4-HYDROXY-1,2-BENZISOTHIAZOLES AND THEIR MANUFACTURE

The present invention relates to 1,2-benzisothiazoles of the general formula (I)

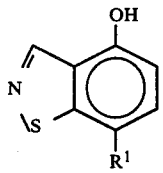

where $R^1$ is hydrogen, amino, which is unsubstituted or substituted by the acyl radical of an organic acid of 1 to 4 carbon atoms, or nitro, and where the phenolic hydroxyl may or may not be etherified by benzyl or esterified by the radical of an organic acid of 1 to 4 carbon atoms.

Accordingly, the invention more particularly relates to 4-hydroxy-1,2-benzisothiazole, 7-nitro-4-hydroxy-1,2-benzisothiazole, 7-amino-4-hydroxy-1,2-benzisothiazole and 7-acetamino-4-hydroxy-1,2-benzisothiazole.

The compounds according to the invention may be manufactured from conventional intermediates by a one-stage of multi-stage reaction sequence, entailing hydrolysis, elimination, reduction, substitution and/or esterification reactions.

Examples of conventional intermediates are 4-chloro-7-nitro-1,2-benzisothiazole, 4-methoxy-7-amino-1,2-benzisothiazole and 4-methoxy-1,2-benzisothiazole, and such intermediates are described, for example, in Liebigs Ann. Chem. 729 (1969), 146–151 and in J. Chem. Soc. London (1971 C), 3994–3999.

7-Nitro-4-hydroxy-1,2-benzisothiazole can be manufactured from 4-chloro-7-nitro-1,2-benzisothiazole by reaction with an alkali metal hydroxide or alkaline earth metal hydroxide, or by treatment with a tertiary amine in the presence of a solvent or diluent, advantageously at from 50° to 150° C. under atmospheric pressure or in a closed vessel under superatmospheric pressure.

The alkali metal hydroxide used in the reaction is preferably sodium hydroxide or potassium hydroxide and the alkaline earth metal hydroxide preferably calcium hydroxide or magnesium hydroxide; these hydroxides are advantageously used in the stoichiometric amount or may be used in excess. Suitable tertiary amines are lower aliphatic amines where alkyl is of 3 to 12 carbon atoms, e.g. trimethylamine, triethylamine and tributylamine, cycloaliphatic amines, e.g. N-methylpiperidine, or pyridine, in particular in aqueous solution. The use of a mixture of an aqueous amine solution, e.g. trimethylamine solution, with a dialkylformamide, ethanol, n-butanol, glycol dimethyl ether or dimethylsulfoxide is preferred.

Advantageous solvents or diluents are water, lower aliphatic alcohols of 1 to 4 carbon atoms, e.g. methanol, ethanol, propanol or n-butanol, dialkylformamides, e.g. dimethylformamide or diethylformamide, glycol ethers, e.g. glycol dimethyl ether, dimethylsulfoxide and mixtures of the said solvents. Amongst these, mixtures of water with dialkylformamides, ethanol, n-butanol, glycol dimethyl ether or dimethylsulfoxide are preferred.

The replacement of the chlorine is preferably carried out at from 70° to 90° C. The reaction may be accelerated, or finished, by heating. As a rule, the reaction is complete after from 1 to 5 hours, depending on the reaction temperature.

7-Amino-4-hydroxy-1,2-benzisothiazole is obtained from 7-nitro-4-hydroxy-1,2-benzisothiazole by reducing the nitro group.

The nitro group is reduced in the conventional manner by means of activated hydrogen in the presence of a metal catalyst in an inert diluent or solvent at room temperature or elevated temperatures of up to 120° C., under atmospheric pressure or pressures of up to 200 bars.

Suitable metal catalysts are Raney nickel, platinum sulfide catalysts and palladium catalysts. The preferred catalyst is palladium on charcoal.

Solvents advantageously used for the hydrogenation are lower alcohols of 1 to 3 carbon atoms, cyclic aliphatic ethers, glycol ethers and mixtures of the said solvents. Amongst these, methanol, ethanol, dioxane, tetrahydrofuran, glycol dimethyl ether and mixtures of these are preferred. Further advantageous solvents are mixtures of a lower carboxylic acid of 2 to 4 carbon atoms with its anhydride, preferably an acetic acid/acetic anhydride mixture, e.g. in the ratio of from 1:1 to 1:2.

As a rule, the reduction of the nitro group is preferably carried out at from 50° to 80° C. under a hydrogen pressure of from 1 to 100 bars.

If a carboxylic acid/carboxylic acid anhydride mixture is used as the diluent or solvent for the hydrogenation, a diacylated end product, e.g. 7-acetamino-4-acetoxy-1,2-benzisothiazole is obtained, which can subsequently be deacylated in the conventional manner to 7-amino-4-hydroxy-1,2-benzisothiazole.

This double deacylation is carried out in solution with water or a lower aliphatic alcohol of 1 to 4 carbon atoms, e.g. methanol, ethanol or butanol, in the presence of a mineral acid, e.g. hydrochloric acid, sulfuric acid or phosphoric acid, or of an organic acid, e.g. p-toluenesulfonic acid or benzoic acid, or of a Lewis acid, e.g. boron trifluoride or zinc chloride, or in the presence of a basic compound, e.g. an alkali metal hydroxide or carbonate, preferably sodium hydroxide or potassium hydroxide.

The mineral acid used is preferably concentrated aqueous hydrochloric acid, which may or may not be mixed with a suitable diluent or solvent. Preferred diluents or solvents are lower aliphatic alcohols of 1 to 4 carbon atoms, water, cyclic ethers, dialkylformamides or dimethylsulfoxide, and amongst these water, methanol, ethanol and dimethylsulfoxide are particularly suitable. The double deacylation is carried out at room temperature or elevated temperatures of up to 130° C., preferably at about 100° C.

It is also possible to carry out a selective deacylation in the conventional manner to give 7-acetamino-4-hydroxy-1,2-benzisothiazole, by carrying out the reaction in the presence of catalytic amounts of a transesterification catalyst, e.g. p-toluenesulfonic acid, an acid ion exchanger, boron trifluoride or sodium borohydride in a lower alcohol, e.g. methanol, ethanol or propanol, at room temperature or preferably at the boil of the alcohol employed as the reactant and diluent or solvent. The use of catalytic amounts of p-toluenesulfonic acid or of sodium borohydride in methanol or ethanol deserves particular mention. As a rule, the amount of p-toluenesulfonic acid used in such cases is from 1 to 10%, based on the weight of the diacyl compound.

Compared to 7-amino-4-hydroxy-1,2-benzisothiazole, 7-acetamino-4-acetoxy-1,2-benzisothiazole is distinguished by increased stability to light and to air and can therefore be used as a storage form of 7-amino-4-hydroxy-1,2-benzisothiazole.

The reduction, described above, to give 7-amino-4-hydroxy-1,2-benzisothiazole can also be carried out with 7-nitro-4-acetoxy-1,2-benzisothiazole, obtained by prior acetylation.

The acetylation of 7-nitro-4-hydroxy-1,2-benzisothiazole to give 7-nitro-4-acetoxy-1,2-benzisothiazole is carried out in the conventional manner with excess acylating agent, for example with acetic anhydride or an acetyl halide, preferably acetyl chloride, at room temperature or by heating, for example at from 40° to 100° C.

The acetylation is advantageously carried out in excess acylating agent, but may also be carried out in an inert organic solvent, for example an aromatic hydrocarbon, e.g. benzene or toluene, an ether, e.g. diethyl ether, dioxane, tetrahydrofuran or glycol dimethyl ether, or an appropriate mixture of these solvents.

Apart from catalytically reducing the 7-nitro group to the amino group, the said nitro group can also be reduced in the conventional manner using other methods applicable to the reduction of nitro groups bonded to aromatic structures. Examples include reductions with hydrazine/Raney nickel, sodium borohydride/cobalt(II) chloride, sulfuretted sodium borohydride, iron carbonyls, e.g. iron pentacarbonyl, and preferably a metal/acid combination, e.g. tin, zinc, iron or aluminum amalgam used together with hydrochloric acid, sulfuric acid or acetic acid, amongst which methods the Bechamp reduction with iron and acetic acid deserves particular mention.

The Bechamp reduction is carried out at room temperature and is preferably accelerated, or finished, by heating, e.g. at from 50° to 150° C.

This reduction is as a rule carried out under atmospheric pressure or in a closed vessel under superatmospheric pressure, with or without simultaneous heating. The reaction may be carried out in the presence of a diluent or solvent, for example, a lower alcohol, e.g. methanol, ethanol or preferably propanol, or in the acid required for the reduction, preferably in acetic acid, or in the acylating reaction medium of acetic acid and acetic anhydride, described above, in which 7-acetamino-4-acetoxy-1,2-benzisothiazole is obtained. 7-Acetamino-4-acetoxy-1,2-benzisothiazole can subsequently be deacylated in the above manner to give 7-amino-4-hydroxy-1,2-benzisothiazole.

The new 4-hydroxy-1,2-benzisothiazole can also be obtained by ether cleavage of a 4-substituted 1,2-benzisothiazole of the general formula (II)

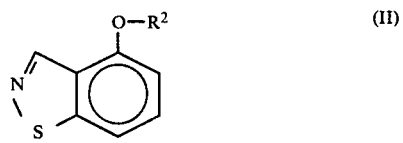

(II)

where $R^2$ is alkyl of 1 to 4 carbon atoms or is α-aralkyl.

Examples of alkyl $R^2$ are methyl, ethyl, propyl and butyl, amongst which methyl is preferred. The preferred α-aralkyl is benzyl.

The ether cleavage is carried out in the conventional manner, using the reagents conventionally employed for such reactions. Specific examples of such reagents are hydrohalic acids, preferably aqueous hydrobromic acid and hydroiodic acid, in the presence or absence of red phosphorus and/or aliphatic carboxylic acids of 1 to 5 carbon atoms, preferably formic acid or acetic acid, as the diluent, or pyridine hydrohalides, e.g. pyridinium chloride or pyridinium bromide, or lithium iodide in collidine, or diborane, aluminum chloride or boron trihalides, preferably boron tribromide, in an aromatic hydrocarbon, e.g. benzene, toluene or xylene.

The ether cleavage reactions may be carried out at room temperature or at elevated temperatures, for example at from 100° to 150° C., under atmospheric pressure, or in a closed vessel under superatmospheric pressure. The reactions can be carried out in an inert diluent or solvent or in a melt of the compound which brings about the ether cleavage, for example in a pyridinium halide melt, advantageously at from 150° to 220° C.

The reaction time depends on the reaction temperature and on the reagent employed for the ether cleavage; in general, the cleavage reactions are complete after about 5 hours. The end product is isolated in the conventional manner, for example by filtering or by distilling off the diluent or solvent or excess reactant. The 4-hydroxy-1,2-benzisothiazole thus obtained is purified in the conventional manner, e.g. by recrystallization from a suitable solvent, by chromatography, or by an extractive partition—utilizing the phenolic properties of 4-hydroxy-1,2-benzisothiazole—between an organic phase and a basic aqueous phase.

4-Methoxy-1,2-benzisothiazole, an example of a compound used for the process of the invention, is described in J. Chem. Soc. London (1971, C), 3994–3999. 4-Benzyloxy-1,2-benzisothiazole and other 4-alkoxy compounds may be obtained, for example, by reductive desamination of the corresponding 7-amino-1,2-benzisothiazoles.

The 7-amino group can be replaced by hydrogen by means of reductive desamination. For example, 4-amino-4-benzyloxy-1,2-benzisothiazole is diazotized in the conventional manner to give the 4-benzyloxy-1,2-benzisothiazole-7-diazonium salt which is then converted to 4-benzyloxy-1,2-benzisothiazole by means of a reducing agent, with elimination of nitrogen.

The diazotization is carried out in an aqueous medium using an alkali metal nitrite, preferably sodium nitrite, in the presence of an acid, e.g. sulfuric acid, hydrochloric acid, phosphoric acid, nitric acid or a mixture of these acids, or using an ester of nitrous acid, preferably ethyl nitrite or amyl nitrite, in an organic solvent, e.g. dimethylformamide, a lower aliphatic alcohol of 1 to 4 carbon atoms, e.g. ethanol or propanol, or glacial acetic acid.

The subsequent replacement of the diazonium group by hydrogen is carried out by means of the conventional reducing agents for this type of reaction, e.g. by means of alcohols, preferably ethanol or benzyl alcohol, by means of ethanol in the presence of metals, e.g. zinc or copper, by means of ethers, preferably tetrahydrofuran, 1,3-dioxolane, dioxane or glycol dimethyl ether, or by means of hypophosphorous acid, alkaline formalin solution, formic acid derivatives, divalent tin compounds, alkaline glucose solutions and salts of sulfurous acid.

The preferred method is to reduce the diazonium compound in a water-soluble ether, of which tetrahydrofuran is a preferred example. The reaction is carried out in the conventional manner by adding an excess amount of the ether to the ice-cold, aqueous acid diazonium salt solution. The evolution of nitrogen is then controlled by adding an aqueous alkali metal acetate solution, whilst thoroughly mixing the batch. The 4-benzyloxy-1,2-benzisothiazole is isolated in the conventional manner, for example by extraction with an organic solvent, e.g. an ether, a halohydrocarbon, preferably methylene chloride or chloroform, or a lower alkyl acetate, e.g. methyl acetate, ethyl acetate or propyl acetate. The solutions obtained are then freed from the diluent or solvent and the residue left is chromatographed or distilled. 7-Amino-4-benzyloxy-1,2-benzisothiazole can be prepared in accordance with the above processes by reducing 7-nitro-4-benzyloxy-1,2-benzisothiazole. 7-Nitro-4-benzyloxy-1,2-benzisothiazole itself is readily obtainable by benzylating 7-nitro-4-hydroxy-1,2-benzisothiazole with a benzyl halide, e.g. benzyl chloride or bromide or benzyl tosylate.

The alkylation reactions at the 4-hydroxyl group can be carried out at slightly elevated temperatures, preferably at from 60° to 120° C., under atmospheric pressure, or, more rapidly, in a closed vessel under superatmospheric pressure. The reactions may be carried out in an inert diluent or solvent, for example a lower aliphatic ketone, e.g. acetone, methyl ethyl ketone or methyl isobutyl ketone, a lower alcohol, e.g. methanol, ethanol, a propanol or a butanol, a lower alkyl acetate, e.g. methyl acetate, ethyl acetate or propyl acetate, a dialkylformamide, e.g. dimethylformamide or diethylformamide, or dimethylsulfoxide, or with an excess of the alkylating agent acting as a diluent or solvent. Preferably, the alkylation is carried out in the presence of a suitable base, such as an alkali metal carbonate, bicarbonate, hydroxide, hydride or alcoholate, a basic oxide, e.g. aluminum oxide or calcium oxide or an organic base, e.g. pyridine, piperidine or a lower trialkylamine, e.g. trimethylamine or triethylamine. Alkyl halides, tosylates and sulfates may be used in the same way as benzyl halides and benzyl tosylate.

4-Hydroxy-1,2-benzisothiazole according to the invention is obtainable not only by the processes described above but also directly from 7-amino-4-hydroxy-1,2-benzisothiazole by reductive desamination. The latter is advantageously carried out by diazotizing, and then reducing the diazonium salt. The diazotization and reduction can be carried out by the methods described above. Preferably, the esters of nitrous acid, e.g. ethyl nitrite, propyl nitrite or amyl nitrite, are used for the diazotization.

The 4-hydroxy-1,2-benzisothiazoles according to the invention, of the general formula (I), are valuable intermediates for the synthesis of pharmacologically active compounds. For example, alkylation of 4-hydroxy-1,2-benzisothiazole with an epihalohydrin or an α,ω-dihalo-2-propanol, followed by reaction with an amine, gives aryloxypropanolamines of the general formula (III)

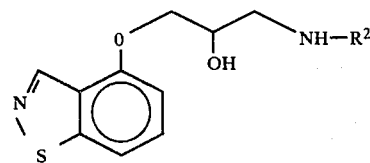
(III)

where $R^2$ is alkyl of 3 to 6 carbon atoms branched at the carbon in the α-position to the nitrogen, or is alkynyl of 3 to 6 carbon atoms, which compounds may be used for treatment and prophylaxis in cardiac and circulatory disorders.

The present invention is illustrated by the Examples which follow.

EXAMPLE 1

43 g of 4-chloro-7-nitro-1,2-benzisothiazole and 16 g of sodium hydroxide powder in 400 ml of ethanol are stirred for 1 hour at 70° C. When the mixture has cooled, 500 ml of water are added, the batch is neutralized with dilute sulfuric acid whilst cooling with ice, and the product which has precipitated is filtered off. The filter cake is then washed with a little ice-cold methanol, and dried. 34 g (86% of theory) of 7-nitro-4-hydroxy-1,2-benzisothiazole are obtained, melting at 284° C. (with decomposition) after one recrystallization from n-butanol.

| $C_7H_4N_2O_3S$ (196) | | | | | |
|---|---|---|---|---|---|
| Calculated: | 42.9 C | 2.0 H | 14.3 N | 24.5 O | 16.3 S |
| Found: | 43.1 C | 2.0 H | 14.3 N | 24.1 O | 16.1 S |

EXAMPLE 2

5.0 g of 7-nitro-4-hydroxy-1,2-benzisothiazole, in a mixture of 50 ml of acetic anhydride, 10 ml of acetic acid and 50 mg of a 5% strength palladium-on-charcoal catalyst, are left for 10 hours at 60° C. under 100 bars hydrogen pressure. After the mixture has cooled, the catalyst is filtered off, the filtrate is concentrated under reduced pressure and the partially crystalline crude product is recrystallized from acetic anhydride. 4.2 g (67% of theory) of 7-acetamino-4-acetoxy-1,2-benzisothiazole of melting point 215°–216° C. are obtained.

| $C_{11}H_{10}O_3N_2S$ (250) | | | | | |
|---|---|---|---|---|---|
| Calculated: | 52.8 C | 4.0 H | 19.2 O | 11.2 N | 12.8 S |
| Found: | 52.6 C | 4.3 H | 19.9 O | 11.1 N | 12.4 S |

EXAMPLE 3

50 g of 7-acetamino-4-acetoxy-1,2-benzisothiazole in a mixture of 250 ml of methanol and 150 ml of concentrated hydrochloric acid are heated for 2 hours under reflux and then freed from volatile constituents by vacuum distillation. The residue which is left is washed with 2 N sodium hydroxide solution and with water, and is dried. 25.6 g (77% of theory) of melting point 205°–206° C. are obtained. The substance is identical with the compound prepared as described in Example 4.

EXAMPLE 4

50 g of 7-nitro-4-hydroxy-1,2-benzisothiazole in 1.5 l of ethanol containing 5 g of 5% strength palladium-on-charcoal catalyst are left for 8 hours at 70° C. under 100 bars hydrogen pressure. When the mixture has cooled, the catalyst is filtered off and the filtrate is evaporated under reduced pressure. 38.5 g of a crystalline residue melting at 190°–192° C. (with decomposition) remain, from which analytically pure 7-amino-4-hydroxy-1,2-benzisothiazole melting at 208°–209° C. is obtained by vacuum sublimation (0.05 mm Hg/140°–160° C.).

| C₇H₆ON₂S (166) | | | | |
|---|---|---|---|---|
| Calculated: 50.6 C | 3.6 H | 9.6 O | 16.9 N | 19.3 S |
| Found: 50.5 C | 4.1 H | 9.9 O | 16.7 N | 19.2 S |

EXAMPLE 5

54 g of 7-nitro-4-hydroxy-1,2-benzisothiazole in 300 ml of acetic anhydride are heated with 0.2 ml of perchloric acid for half an hour on a steam bath. After the mixture has stood for one hour, about 150 ml of the volatile constituents are distilled off and on filtering off the crystalline constituent 50 g (75% of theory) of 7-nitro-4-acetoxy-1,2-benzisothiazole of melting point 117°–118° C. are obtained.

| C₉H₆O₄N₂S (238) | | | | |
|---|---|---|---|---|
| Calculated: 45.4 C | 2.5 H | 26.9 O | 11.8 N | 13.5 S |
| Found: 45.6 C | 2.6 H | 27.2 O | 11.8 N | 13.2 S |

EXAMPLE 6

7.0 g of 7-acetamino-4-acetoxy-1,2-benzisothiazole in 80 ml of ethanol containing 0.4 g of p-toluenesulfonic acid are refluxed for 100 hours. The volatile constituents are then distilled off under reduced pressure and the residue is recrystallized from a mixture of ethanol and benzene. 2.5 g (43% of theory) of 7-acetamino-4-hydroxy-1,2-benzisothiazole of melting point 234°–236° C. remain.

| C₉H₈O₂N₂S (208) | | | | |
|---|---|---|---|---|
| Calculated: 51.9 C | 3.9 H | 15.4 O | 13.5 N | 15.4 S |
| Found: 52.9 C | 4.0 H | 15.5 O | 13.2 N | 15.0 S |

EXAMPLE 7

20 g of 7-nitro-4-acetoxy-1,2-benzisothiazole in 200 ml of ethanol are hydrogenated with 2 g of Raney nickel at room temperature for 65 hours under atmospheric pressure. After filtering off the catalyst, the batch is concentrated to 50 ml under reduced pressure, 100 ml of acetic anhydride are added and the mixture is boiled up briefly and poured, after cooling, onto 400 g of ice. After filtration, the filter residue is extracted with a mixture of ethanol and chloroform and the extract is dried over magnesium sulfate. The solution is concentrated and the syrupy crude product is mixed with a little methanol. This gives 17.5 g (83% of theory) of 7-acetamino-4-acetoxy-1,2-benzisothiazole of melting point 215°–216° C., which is identical with the compound prepared as described in Example 2.

EXAMPLE 8

7 g of zinc dust are added in 15 portions to 50 g of 7-nitro-4-1,2-benzisothiazole in a mixture of 20 ml of acetic acid and 20 ml of acetic anhydride and the mixture is then boiled up briefly. When it has cooled, the inorganic material is filtered off and the filter residue is washed with a little water and then repeatedly with cold ethanol. The combined organic solutions are concentrated under reduced pressure. The residue crystallizes after a few hours and 3.7 g (70% of theory) of 7-acetamino-4-acetoxy-1,2-benzisothiazole of melting point 216°–217° C., identical with the material prepared as described in Example 2, are obtained.

EXAMPLE 9

50 g of 4-methoxy-1,2-benzisothiazole are suspended in 700 ml of acetic acid containing 10% by weight of hydrogen bromide and 5 g of red phosphorus, and the suspension is heated in a tantalum autoclave at 100° C. for 30 hours. When it has cooled, the product is concentrated under reduced pressure and the residue is partitioned between methylene chloride and 2 N sodium hydroxide solution. The aqueous phase is freed from insoluble matter by filtration, and is washed with methylene chloride, acidified with hydrochloric acid and finally extracted repeatedly with methylene chloride. The combined extracts are dried over magnesium sulfate and concentrated under reduced pressure. 32 g (65% of theory) of 4-hydroxy-1,2-benzisothiazole of melting point 133°–134° C. are obtained.

| C₇H₅ONS (151) | | | | |
|---|---|---|---|---|
| Calculated: 55.6 C | 3.3 H | 10.6 O | 9.3 N | 21.2 S |
| Found: 56.1 C | 3.4 H | 10.5 O | 9.1 N | 20.8 S |

If the methylene chloride phases which have been washed with 2 N sodium hydroxide solution are worked up in the conventional manner, it is possible to recover 20–25% of the 4-methoxy-1,2-benzisothiazole employed, which can be recycled to a further ether cleavage reaction.

EXAMPLE 10

10 g of 4-benzyloxy-1,2-benzisothiazole and 50 g of pyridinium chloride are heated at 200° C. for 3 hours. When the melt has cooled, it is dissolved in dilute sulfuric acid and repeatedly extracted with methylene chloride. The combined extracts are dried over magnesium sulfate and concentrated under reduced pressure. This gives 4.8 g (77% of theory) of 4-hydroxy-1,2-benzisothiazole, identical with the compound prepared as described in Example 9.

EXAMPLE 11

54 g of 7-amino-4-benzyloxy-1,2-benzisothiazole are suspended in 400 ml of half-concentrated hydrochloric acid and diazotized at from 0° to 5° C. with a solution of 16 g of sodium nitrite in 60 ml of water. 500 ml of tetrahydrofuran, 400 ml of a saturated sodium acetate solution and 120 g of sodium acetate are then added and the mixture is allowed to warm up to room temperature. The two-phase reaction medium is then repeatedly extracted with methylene chloride. The combined extracts are dried over magnesium sulfate and then free from solvent under reduced pressure. The crude product is fractionated, giving 30 g (60% of theory) of 4-benzyloxy-1,2-benzisothiazole of melting point 47°–49° C. (boiling point 165° C./0.4 mm Hg).

| C₁₄H₁₁ONS (241) | | | | |
|---|---|---|---|---|
| Calculated: 69.7 C | 4.6 H | 6.6 O | 5.8 N | 13.3 S |
| Found: 70.2 C | 4.9 H | 6.7 O | 5.8 N | 13.0 S |

EXAMPLE 12

28.6 g of 7-nitro-4-benzyloxy-1,2-benzisothiazole are added in portions to a boiling mixture of 67 ml of water, 30 g of iron powder, 3 ml of glacial acetic acid and 167 ml of n-propanol and the mixture is then refluxed for a further hour. When it has cooled, it is neutralized with concentrated ammonia solution and filtered. The filter residue is washed with methylene chloride and the combined wash solutions are dried over magnesium sulfate and freed from the solvent under reduced pressure. 25.1 g (100% of theory) of 7-amino-4-benzyloxy-1,2-benzisothiazole of melting point 126°–128° C. are obtained.

$C_{14}H_{12}ON_2S$ (256)

| | | | | | |
|---|---|---|---|---|---|
| Calculated: | 65.6 C | 4.7 H | 6.2 O | 10.9 N | 12.8 S |
| Found: | 65.8 C | 5.0 H | 6.5 O | 11.2 N | 12.3 S |

EXAMPLE 13

200 g of 7-nitro-4-hydroxy-1,2-benzisothiazole, 260 g of benzyl bromide and 210 g of potassium carbonate in 2.5 l of acetone are refluxed for 12 hours. The entire mixture is then concentrated to one liter under reduced pressure, the residue is poured into a threefold amount of water and the batch is repeatedly extracted with methylene chloride. The combined organic phases are dried over magnesium sulfate and freed from solvent under reduced pressure. The crude product is recrystallized from a mixture of methanol and tetrahydrofuran. 200 g (70% of theory) of 7-nitro-4-benzyloxy-1,2-benzisothiazole of melting point 158°–160° C. are obtained.

$C_{14}H_{10}O_3N_2S$ (286)

| | | | | | |
|---|---|---|---|---|---|
| Calculated: | 58.7 C | 3.5 H | 16.8 O | 9.8 N | 11.2 S |
| Found: | 58.7 C | 3.9 H | 16.8 O | 10.0 N | 11.4 S |

EXAMPLE 14

15.1 g of 7-amino-4-hydroxy-1,2-benzisothiazole are slowly suspended in 30 ml of concentrated hydrochloric acid and diazotized with 15 ml of amyl nitrite at from 0° to 5° C. After slowly heating the mixture to 60° C., 18 g of zinc dust are added in 10 portions and the mixture is refluxed until the evolution of gas has ceased. When the mixture has cooled, it is filtered through Celite and the filtrate is partitioned between dilute sodium hydroxide solution and chloroform. After acidifying the aqueous phase and repeatedly extracting it with methylene chloride, the combined organic extracts are dried over magnesium sulfate and freed from the solvent. This gives from 2 to 3 g of 4-hydroxy-1,2-benzisothiazole, which is identical with the compound prepared as described in Example 9.

The following are examples of compounds of the general formula III and/or of their acid addition salts with a physiologically safe acid: 4-(2-hydroxy-3-isopropylamino-propoxy)-1,2-benzisothiazole (III), 4-(2-hydroxy-3-tert.-butylaminopropoxy)-1,2-benzisothiazole (IV), 4-[2-hydroxy-3-(3-methylpentyl-3-amino)-propoxy]-1,2-benzisothiazole (VII), 4-[2-hydroxy-3-(2-methyl-butyl-2-amino)-propoxy]-1,2-benzisothiazole (VI), 4-[2-hydroxy-3-(2-methyl-3-but-2-ynylamino)-propoxy]-1,2-benzisothiazole (VIII), 4-(2-hydroxy-3-sec.-butylaminopropoxy-1,2-benzisothiazole (V), 4-[2-hydroxy-3-(1-methoxy-propyl-2-amino)-propoxy]-1,2-benzisothiazole (IX) and 4-[2-hydroxy-3-(pentyl-2-amino)-propoxy]-1,2-benzisothiazole (X). Because of their $\beta$-sympatholytic action these may in particular be used for the treatment of coronary diseases of the heart, of cardiac arrythmias and of hypertonia. The superior effectiveness of these compounds may be seen from the test report which follows. As is apparent from the Table which follows, the $\beta$-sympatholytic action was tested on rats, in comparison with the known $\beta$-sympatholytic agent Propranolol.

The following methods were used:

1. $\beta_1$-sympatholytic action

Isoproterenol (0.1 µg/kg, given intravenously) in pithed rats (Sprague-Dawley, Mus rattus; weight 230–280 g) causes increases in pulse rate of, on average, 45%. $\beta$-Sympatholytic agents inhibit such tachycardia. Isoproterenol was administered before, and 5 minutes after, the intravenous administration of the test substances. Linear relationships are found between the logarithms of the administered doses (mg/kg) of the test substances and the inhibition (in %) of Isoproterenol trachycardia. From these relationships, the ED 50 values, i.e., the doses which inhibit the Isoproterenol tachycardia by 50%, are determined.

2. $\beta_2$-sympatholytic action

The inhibition, by $\beta$-sympatholytic agents, of the reduction in blood pressure induced by Isoproterenol was tested on rats, weighing 230–280 g, under urethane narcosis (1.78 g of urethane/kg being administered intraperitoneally). Isoproterenol (0.215 µg/kg given intravenously) reduces the mean pressure of the carotid artery by an average of 30%. $\beta$-Sympatholytic agents inhibt this action.

Linear relationships exist between the logarithms of the doses used and the inhibition of the Isoproterenol blood pressure reduction, from which the ED 50 values, i.e., the doses which inhibit the Isoproterenol blood pressure reduction by 50%, were determined.

3. Acute toxicity

The acute toxicity was determined on groups of 10 or 20 female Swiss mice weighing 20–26 g, the compounds being administered intraperitoneally. The LD 50 was taken to be the calculated dose (Probit analysis) after which 50% of the animals died within 24 hours.

Table 1 shows that the pharmacotherapeutically important $\beta_1$-sympatholytic activity of the compounds is from 2.5 to 8 times greater than that of the comparative substance Propranolol. In addition, the substances exhibit a great cardioselectivity than Propranolol, i.e., the pharmacotherapeutically desirable effect on cardiac $\beta_1$-receptors manifests itself at lower doses than the effect of the $\beta_2$-receptors on the blood vessels. In the case of Propranolol, about equal doses are required for both these inhibiting effects. The test substances block cardiac $\beta_1$-receptors at doses which are from 2 to 11 times lower than those required to block $\beta_2$-receptors.

The therapeutic range, expressed as the quotient of the 50% lethal dose (LD 50) and the 50% $\beta_1$-blocking dose (ED 50) is from 3 to 11 times greater than for Propranolol.

TABLE 1

β-Sympatholytic action and acute toxicity

| Example No. | β₁-Sympatholytic action(1) ED 50(2) | β₁-Sympatholytic action(1) R.A.(3) | β₂-Sympatholytic action(4) ED 50(5) | β₂-Sympatholytic action(4) R.A.(3) | Q(6) | Acute toxicity LD 50(7) | Therapeutic range(8) absolute | Therapeutic range(8) relative(9) |
|---|---|---|---|---|---|---|---|---|
| III | 0.00190 | 6.47 | 0.00420 | 2.71 | 2.21 | 62.1 | 32,700 | 3.72 |
| IV | 0.00163 | 7.55 | 0.00402 | 2.84 | 2.47 | 154 | 94,500 | 10.76 |
| V | 0.00153 | 8.04 | 0.0106 | 1.08 | 6.93 | 96.4 | 63,000 | 7.18 |
| VI | 0.00184 | 6.68 | 0.00824 | 1.38 | 4.48 | 144 | 78,300 | 8.92 |
| VII | 0.00328 | 3.75 | 0.0121 | 0.94 | 3.69 | 128 | 39,000 | 4.44 |
| VIII | 0.00230 | 5.35 | 0.00575 | 1.98 | 2.50 | 184 | 80,000 | 9.11 |
| IX | 0.00495 | 2.48 | 0.0440 | 0.26 | 8.90 | 135 | 27,300 | 3.11 |
| X | 0.00252 | 4.88 | 0.0270 | 0.42 | 10.70 | 60.3 | 23,900 | 2.72 |
| Propranolol | 0.0123 | 1.00 | 0.0114 | 1.00 | 0.93 | 108 | 8,780 | 1.00 |

(1) Inhibition of Isoproterenol tachycardia (IT). Pithed rats. Intravenous administration
(2) Dose (mg/kg) which inhibits the IT by 50%
(3) Relative activity. Propranolol = 1.00
(4) Inhibition of Isoproterenol blood pressure reduction (IBP). Rats under urethane narcosis. Intravenous administration.
(5) Dose (mg/kg) which inhibits the IBP by 50%
(6) $Q = \dfrac{\text{ED 50 for } \beta_2\text{-sympatholysis}}{\text{ED 50 for } \beta_1\text{-sympatholysis}}$
(7) Mice, intraperitoneal administration
(8) $\dfrac{\text{LD 50}}{\text{ED 50 (IT)}}$
(9) Propranolol = 1.00

Chemotherapeutic agents or formulations which contain a compound of the formula III as the active ingredient, together with conventional excipients and diluents, are prepared in the conventional manner, and containing an appropriate dosage, using the conventional excipients or diluents and the conventional pharmaceutical auxiliaries, in accordance with the desired method of administration.

Suitable individual doses of these compounds are, in the case of man, from 1 to 100 mg, preferably from 3 to 50 mg.

Examples of further conversions of the compounds according to the invention.

EXAMPLE I 1-(1,2-Benzisothiazol-4-yloxy)-2,3-epoxy-propane 29 g of 4-hydroxy-1,2-benzisothiazole, 36 g of epibromohydrin and 93 g of dry potassium carbonate in 300 ml of acetone are refluxed for 11 hours. After cooling, the entire reaction mixture is poured into 1 liter of ice water and is extracted with four times 150 ml of diethyl ether, and the combined extracts are washed with water and dried over sodium sulfate. After distilling off the solvent, 30 g (75% of theory) of 1-(1,2-benzisothiazol-4-yloxy)-2,3-epoxy-propane of melting point 85°–87° C. remain; this material can be used further without purification.

Analytically pure 1-(1,2-benzisothiazol-4-yloxy)-2,3-epoxypropane of melting point 90°–91° C. is obtained by sublimation at from 110° to 130° C. under 0.2 mm Hg.

| $C_{10}H_9O_2NS$ (207) | | | | | | | |
|---|---|---|---|---|---|---|---|
| Calculated: | 58.0 C | 4.4 H | 15.4 O | 6.8 N | 15.5 S |
| Found: | 57.7 C | 4.6 H | 15.4 O | 6.8 N | 15.1 S |

EXAMPLE II 1-(1,2-Benzylisothiazol-4-yloxy)-3-chloro-propan-2-ol (a) 2.0 g of 1-(1,2-benzisothiazol-4-yloxy)-2,3-epoxypropane are suspended in a mixture of 30 ml of ethanol and 30 ml of diethyl ether and 100 ml of a solution of hydrogen chloride in ether are added whilst stirring. After standing for three days, the precipitate formed is filtered off and washed neutral with ether.

Yield: 2.2 g (91% of theory) of melting point 90°–92° C. Recrystallization from methanol gives 1-(1,2-benzisothiazol-4-yloxy)-3-chloro-propan-2-ol which is pure according to NMR spectroscopy and has a melting point of 104°–106° C.

$^1$H-NMR spectrum (d$_6$-DMSO, TMS as internal standard): τ=0.82 (s, 1H), 2.22 (d, J=4.5 Hz, 1H, 2.42 (m, 1H), 2.99 (d, J=3.0 Hz, 1H), 3.62 (s, OH), 5.73 (m, 3H), 6.11 (m, 2H).

(b) 15.0 g of 4-hydroxy-1,2-benzisothiazole and 100 mg of 2,2,6,6-tetra-methylpiperidine, together with 30 ml of epichlorohydrin, are heated for 6 hours at 100°–110° C. The mixture is then freed from excess epichlorohydrin under reduced pressure and the residue is digested with three times 100 ml of methanol. The combined methanol extracts are evaporated to dryness under reduced pressure. This leaves 10.4 g of semi-crystalline residue, of which the $^1$H-NMR spectrum agrees with that of the 1-(1,2-benzisothiazol-4-yloxy)-3-chloro-propan-2-ol obtained as described in a).

(c) 30.0 g of 4-hydroxy-1,2-benzisothiazole are suspended in 26.0 g of 1,3-dichloro-propanol-2 and a solution of 8.5 g of sodium hydroxide in 60 ml of water is added in the course of 4 hours at from 60° to 80° C. After reacting for a further four hours at the same temperature, the organic phase is taken up in methylene chloride, dried over magnesium sulfate and evaporated to dryness. The residue left (35 g) is recrystallized from methanol. The 1-(1,2-benzisothiazol-4-yloxy)-3-chloro-propan-2-ol obtained is identical with the sample prepared as described in a).

EXAMPLE III 50 g of 1-(1,2-benzisothiazol-4-yloxy)-2,3-epoxypropane and 25 ml of isopropylamine in 50 ml of ethanol are refluxed for 2 hours. The residue which remains after distilling off the solvent and excess amine is dissolved in 5 ml of ethanol and a solution of hydrochloric acid in ether is added dropwise. The 4-(2-hydroxy-3-isopropylaminopropoxy)-1,2-benzisothiazole hydrochloride which precipitates is filtered off, washed with dry ether and dried.

Yield: 6.0 g (83% of theory), of melting point 158°–160° C.

epoxy-propane and the corresponding amines, by the method described in Example III.

| Example No. | —R | Acid component | Melting point °C. | |
|---|---|---|---|---|
| V | —CH(CH$_3$)(C$_2$H$_5$) | COOH\|COOH | 146–148 | 4-(2-Hydroxy-3-sec.-butylamino-propoxy)-1,2-benzisothiazole |
| VI | —C(CH$_3$)(CH$_2$—CH$_3$)(CH$_3$) | HCl | 182–184 | 4-[2-Hydroxy-3-(2-methyl-butyl-2-amino)-propoxy]-1,2-benzisothiazole |
| VII | —C(C$_2$H$_5$)(CH$_3$)(C$_2$H$_5$) | HCl | 180–182 | 4-[2-Hydroxy-3-(3-methyl-pentyl-3-amino)-propoxy]-1,2-benzisothiazole |
| VIII | —C(CH$_3$)(C≡CH)(CH$_3$) | HCl | 151–153 | 4-[2-Hydroxy-3-(2-methyl-3-but-2-ynlamino)propoxy] 1,2-benzisothiazole |
| IX | —CH(CH$_2$OCH$_3$)(CH$_3$) | COOH\|COOH | 152–156 | 4-[2-Hydroxy-3-(1-methoxy-propyl-2-amino)-propoxy]-1,2-benzisothiazole |
| X | —CH(CH$_3$)(CH$_2$—CH$_2$—CH$_3$) | HOOC—COOH | 154–156 | 4-[2-Hydroxy-3-(pentyl-2-amino)-propoxy]-1,2-benzisothiazole |

| C$_{13}$H$_{19}$O$_2$N$_2$SCl (303) | | | | | | |
|---|---|---|---|---|---|---|
| Calculated: | 51.6 C | 6.3 H | 10.6 O | 9.3 N | 10.6 S | 11.7 Cl |
| Found: | 51.4 C | 6.5 H | 11.4 O | 9.4 N | 10.2 S | 11.5 Cl |

EXAMPLE IV 6.3 g (80% of theory) of 4-(2-hydroxy-3-tert.-butylaminopropoxy)-1,2-benzisothiazole hydrochloride of melting point 190°–192° C. are obtained from 50 g of 1-(1,2-benzisothiazol-4-yloxy)-2,3-epoxy-propane and 25 ml of tert.-butylamine by the method described in Example 1.

| C$_{14}$H$_{21}$O$_2$N$_2$SCl (317) | | | | | | |
|---|---|---|---|---|---|---|
| Calculated: | 53.1 C | 6.7 H | 10.1 O | 8.8 N | 10.1 S | 11.2 Cl |
| Found: | 52.7 C | 6.5 H | 10.5 O | 8.7 N | 10.0 S | 11.3 Cl |

The compounds shown in the Table which follows are obtained from 1-(1,2-benzisothiazol-4-yloxy)-2,3-

We claim:
1. 1,2-benzisothiazoles of the formula (I)

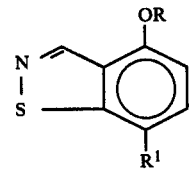

where R$^1$ is hydrogen, amino, which is unsubstituted or substituted by the acyl radical of a carboxylic acid of 1 to 4 carbon atoms, or nitro, and where R is hydrogen, benzyl, or the acyl radical of a carboxylic acid of 1 to 4 carbon atoms.
2. 4-Hydroxy-1,2-benzisothiazole.
3. 7-Nitro-4-hydroxy-1,2-benzisothiazole.
4. 7-Amino-4-hydroxy-1,2-benzisothiazole.
5. 7-Acetamino-4-hydroxy-1,2-benzisothiazole.
6. A 1,2-benzisothiazole as set forth in claim 1, wherein the carboxylic acid is acetic acid.

* * * * *